United States Patent
Dana, III

(10) Patent No.: US 7,448,989 B2
(45) Date of Patent: Nov. 11, 2008

(54) MALE EXERCISE DEVICE

(76) Inventor: Alfred Dana, III, 2805 E. Oakland Park Blvd., #222, Ft. Lauderdale, FL (US) 33306

( * ) Notice: Subject to any disclaimer, the term of this patent is extended or adjusted under 35 U.S.C. 154(b) by 0 days.

(21) Appl. No.: 11/499,313

(22) Filed: Aug. 4, 2006

(65) Prior Publication Data
US 2006/0270533 A1 Nov. 30, 2006

(51) Int. Cl.
*A63B 21/065* (2006.01)
*A63B 21/06* (2006.01)
*A61F 5/00* (2006.01)

(52) U.S. Cl. .............................. 482/105; 482/93; 600/38
(58) Field of Classification Search ................. 482/121, 482/127–128, 44, 48–50, 93, 105; 600/38–41
See application file for complete search history.

(56) References Cited

U.S. PATENT DOCUMENTS

| | | | |
|---|---|---|---|
| 867,340 A | 10/1907 | Barrie | |
| 3,926,184 A * | 12/1975 | Gehl | 600/41 |
| 5,060,934 A * | 10/1991 | Winston | 482/49 |
| 5,224,914 A * | 7/1993 | Friedman | 482/127 |
| 5,526,803 A * | 6/1996 | Kelly | 128/95.1 |
| 5,702,330 A * | 12/1997 | De Monbrun et al. | 482/105 |
| 5,800,340 A * | 9/1998 | Gekhter et al. | 600/39 |
| 6,080,090 A * | 6/2000 | Taylor et al. | 482/121 |
| 7,041,041 B1 * | 5/2006 | Evans | 482/126 |

* cited by examiner

*Primary Examiner*—Fenn C Mathew
(74) *Attorney, Agent, or Firm*—Richard M. Saccocio

(57) ABSTRACT

An exercise device for strengthening and enlargement of the penis includes flexible members, such as straps or pads, adapted to fit around an erect penis and spaced along the length of the penis. An elongated member is attached at one end to each of the straps or pads and extend downward therefrom. The other end of the elongated members are each attached to an opposite end of a spring member. The opposite end portions of the spring member comprise lever arms. A weight member is attachable to the spring member at a location approximately equidistant between the ends of the spring member. Each attachment joint of the elongated members, the spring member and the weight allows for relative pivoting, rotation or bending at each of the joints.

15 Claims, 4 Drawing Sheets

MALE EXERCISE DEVICE

This application claims the benefit under 35 U.S.C. 120, of the earlier filing date of U.S. application Ser. No. 10/693,168, entitled "Male Exercise Device", by Alfred Dana III, filed on Oct. 23, 2003

BACKGROUND OF THE INVENTION

A. Area of Invention

The present invention relates to a male exercise device.

B. Prior Art

As is set forth in U.S. Pat. No. 5,702,330 (1997) to De Monbrun et ual, entitled Male Exercise Device and Method, a form of exercise, known as Kegel exercise, was developed by a Dr. Arnold Kegel as a way of helping women regain control of urination after child birth. Such exercises are effective in restoring muscle tone in the perinea area and, in particular, the pubococcygeus muscle. However, many of those who practice the Kegel exercises regularly reported an increase in sensation during intercourse as well as an increase in general sensitivity. See Kegel, A., "Sexual Functions of the Pubococcygeus Muscle." Western Journal of Surgery, Vol. 60, pp 521-524 (1952).

In recent years, Kegel exercises have been adapted for males with similar results. Therein, the portion of the penis which extends internally into the male pelvic cavity is surrounded by an extensive network of muscles, the most important of which is the pubococcygeus muscle. In most men, these muscles are quite weak, and strengthening of these muscles may be achieved by performing Kegel exercises. This has resulted in reports of male benefits including stronger and more pleasurable orgasms, better ejaculatory control, and increased pelvic sensation during sexual arousal. See, for example, Crooks and Baur, Our Sexuality, 4.sup.th Ed. (1990) The Benjamin/Cummings Publishing Company and Zilbergeld, Male Sexuality, 1978, Little, Brown & Company.

A suggested Kegel exercise program was outlined in Cooks and Bauer above, at Page 160. This program involves the performing of a series of so-called "short Kegels," i.e., holding a contraction of each Kegel, wherein the number of such short Kegels is gradually increased until one can comfortably perform several dozen at a time, twice daily. Thereafter, "long Kegels" are practiced by holding each contraction for a count of three. Eventually, short and long Kegels in each daily exercise routine are combined, and done twice daily. A male may locate the pubococcygeus muscle by squeezing his pelvic muscle during urination to stop the flow of urine several times. The muscles which are squeezed to accomplish this are the ones which are then used to perform the Kegel exercises. If the correct male Kegel exercise is performed while not urinating, the penis will move slightly upward. Kegel exercises done with a penile erection will cause the penis to move up and down.

The prior art, as reflected in De Monbrun above, is directed to a particular exercise device and method of use thereof, intended to further the historic purpose of male Kegel exercises, that is, stronger and more pleasurable orgasms, better ejaculatory control, and increased pelvic sensation. Said art however does not seek to necessarily strengthen or enlarge the penis.

For many who undertake the time and inconvenience of Kegel exercises, the within invention confers additional benefits if an appropriate exercise device is employed upon the penis during the performance of Kegel and related exercises. Further, traditional Kegel exercises, inclusive of that method taught by said prior art to De Monbrun, are generally directed to males suffering from a weakness in the pubococcygeus muscle which consequently reduces or diminishes some aspect of sexual function. In distinction, the present system has been specifically developed for use by the healthy adult male wishing to strengthen and/or enlarge his penis.

SUMMARY OF THE INVENTION

An exercise device for strengthening and enlargement of the penis includes flexible members, such as straps or pads, adapted to fit around an erect penis and spaced along the length of the penis. An elongated member is attached at one end to each of the straps or pads and extend downward therefrom. The other end of the elongated members are each attached to an opposite end of a spring member. The opposite end portions of the spring member comprise lever arms. A weight member is attachable to the spring member at a location approximately equidistant between the ends of the spring member. Each attachment joint of the elongated members, the spring member and the weight allows for relative pivoting, rotation or bending at each of the joints.

With the exercise device in place, a Kegel contraction or penis flexing is effectuated which causes the penis to rise upward relative to its previous substantially horizontal position. The flexibility of each joint and the bending of the lever arms of the spring member provides for the repositioning of the weight relative to its initial position to the penis. Upon relaxing of the contraction, the weight member returns to its initial position, thereby providing for consistent and controllable exercising. During the contractions and relaxings, the lever arms of the spring will alternatively bend or rotate up and down causing the weight to undergo a beneficial "bounce" effect which is transmitted to and strengthens the muscles being exercised It is an object of the present invention to provide an improved male exercise device for the strengthening and enlargement of the penis.

It is a further object of the invention to provide a device of the above type useful in a virility enhancement system for use by healthy adult males.

It is a still further object to provide a device having particular utility in an exercise program for the entire group of male abdominal muscles.

It is a still further object to provide a device having particular utility in an exercise program for the strengthening of muscles of the base of the penis and muscles behind the glans of the penis.

The above and yet other objects and advantages of the present invention will become apparent from the hereinafter set forth Brief Description of the Drawings, Detailed Description of the Invention and claims appended herewith.

DETAILED DESCRIPTION OF THE INVENTION

Figure 1:
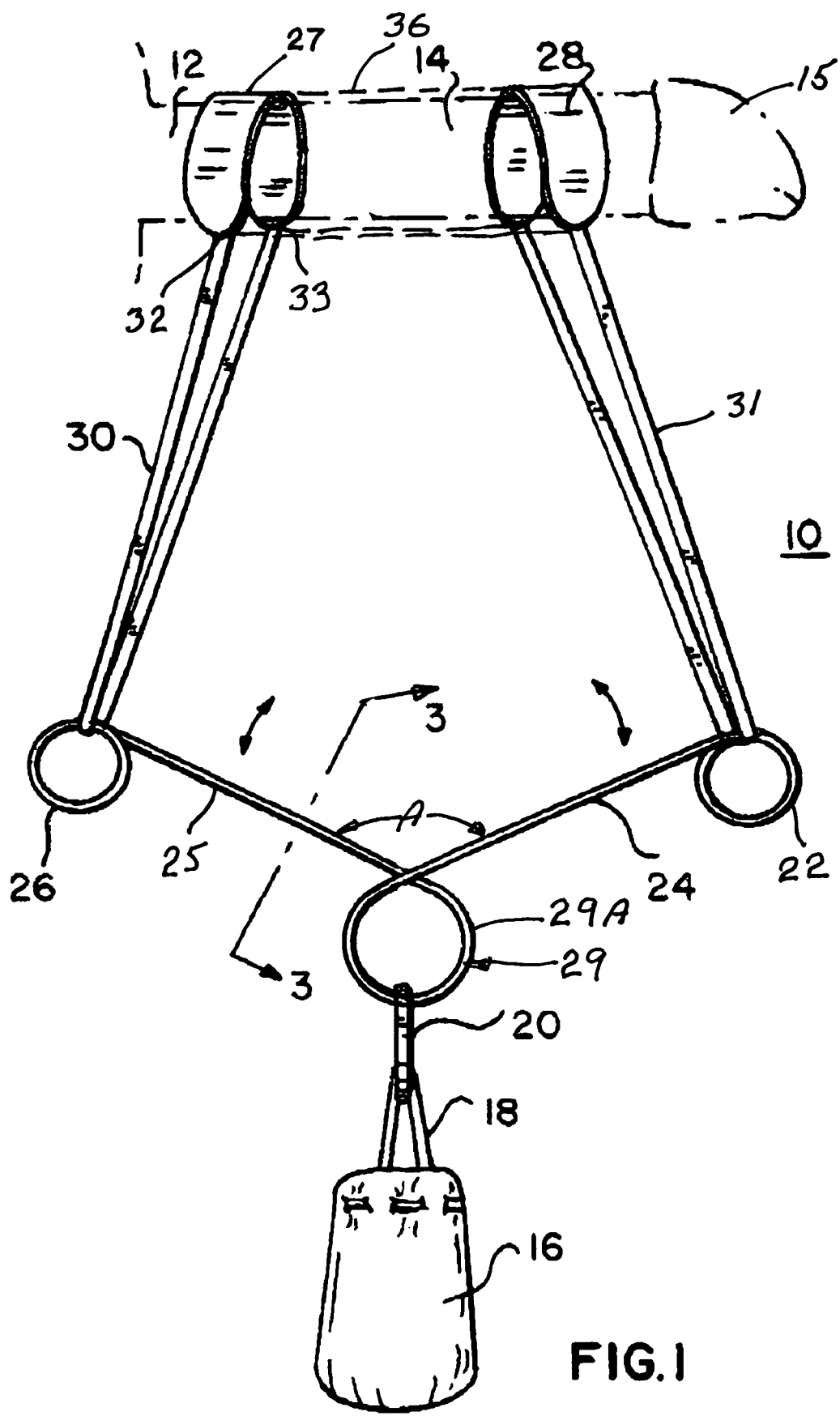
FIG. 1 is a front elevational view of the inventive exercise device attached to an erect penis when unflexed.

With reference to the front elevational view of FIG. 1, an inventive male exercise device 10 may be seen to include first and second flexible elongate pads 27 and 28, each having a width and length proportioned for engagement about an erect penis 14. Therein, a first flexible pad 27 is positioned proximally to base 12 of the penis while a second pad 28 is positioned proximally to glans 15 of the erect penis 14. Pads 27 and 28 can simply comprise a length of cloth or the like having sufficient padding so as to not cause any undue discomfort to the penis 14 when the exercise device 10 is positioned on the penis 14. As an alternative to individual pads 27 and 28, a single piece of padding 36 can be used that extends the length of in place pads 27 and 28, as seen in phantom in FIG. 1.

Ends of said elongate pads 27 and 28 are secured to penis 14 by respective first and second cords 30 and 31. In the preferred embodiment, cords 30 and 31 are flexible. More particularly, opposing ends 32 and 33 of each cord 30 and 31 depend from opposite elongate ends of the respective pads 27 and 28. At substantially the center of each flexible cord 30 and 31, said cords pass through retaining means 22 and 26 of respective first and second lever arms 24 and 25 of a central spring section 29 of the device. The configuration of central spring section 29 may be more fully seen with reference to the cross-sectional view of FIG. 3.

Figure 1A:
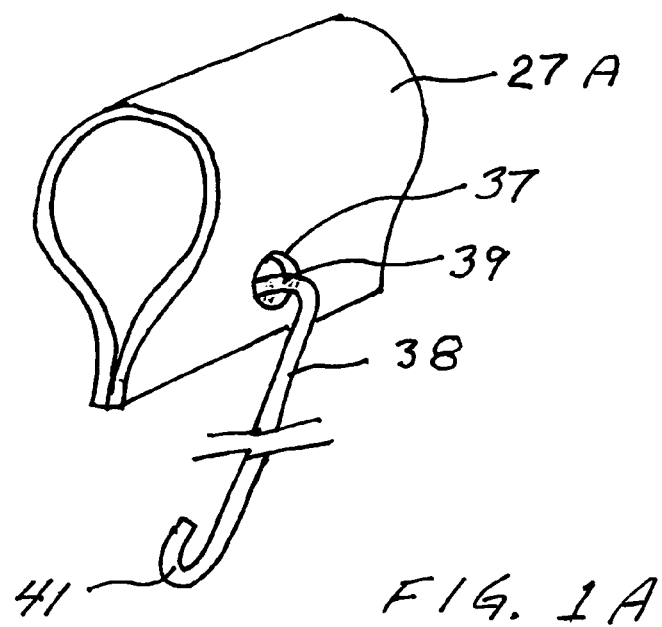
FIG. 1A illustrates another embodiment of the member attaching the exercise device to a penis.

FIG. 1A illustrates an alternative embodiment of the cords 30 and 31 and pads 27 and 28 seen in FIG. 1. In this embodiment, the configuration of the pad 27A is such that it extends below the underside of the penis having a hole 37 through both ends thereof. In place of the double stranded cords 30 and 31, a single stranded cord 38 is used. Cord 38 can comprise a relatively non-flexible or semi-flexible rod having an integral hook 39 and 41 at opposite ends thereof. Thus, cord 38 can comprise a molded plastic rod or even a metal rod. The hook 39 is used to make the attachment to pad 27A through holes 37 and provide a relatively friction free joint or one that allows for easy relative movement at the joint. Similarly, the hook 41 at the opposite end of cord 38 can be used to effectuate a joint to the retaining means 26 of the lever arm 25 of spring 29.

Figure 2:
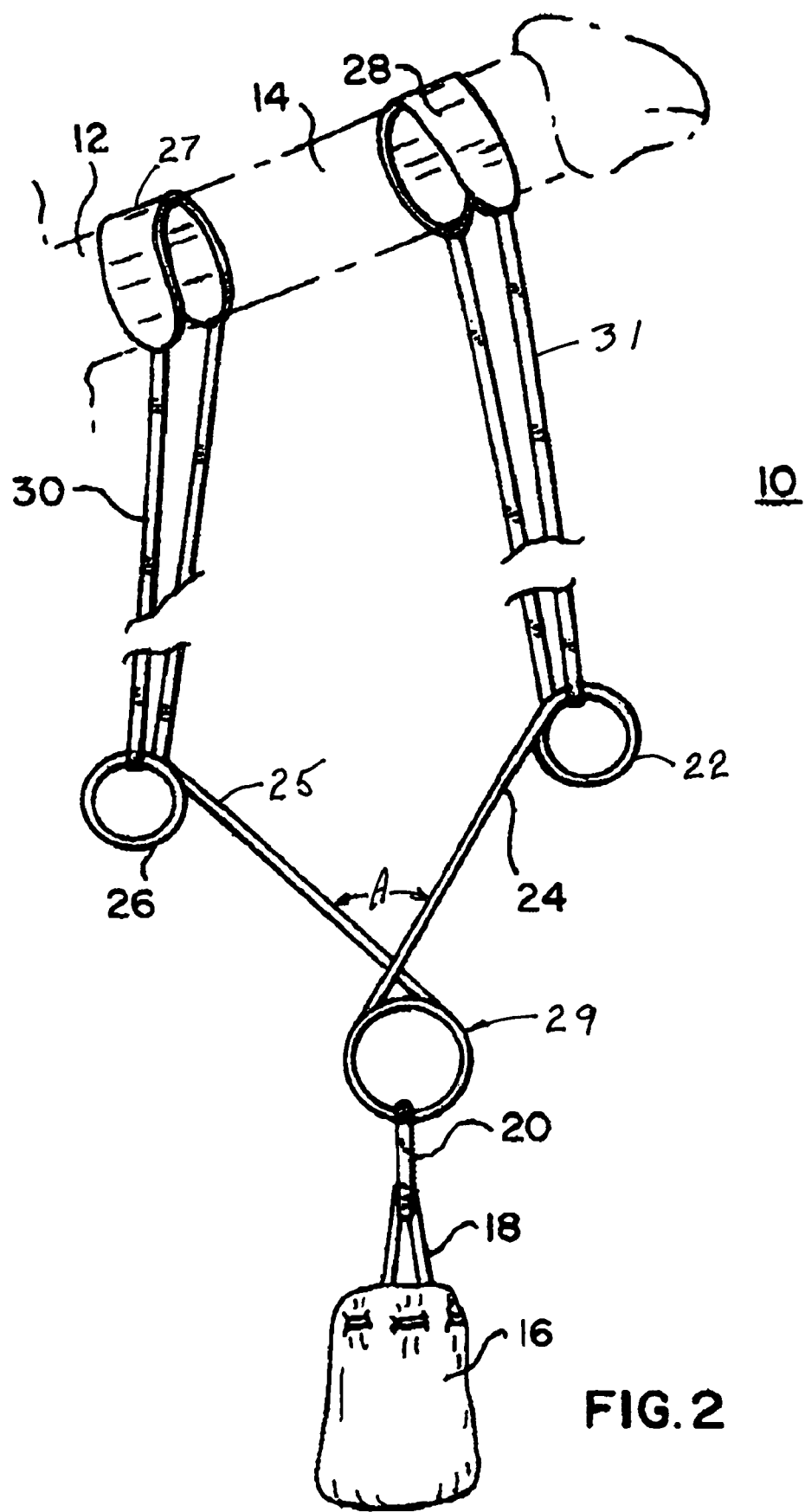
FIG. 2 is a view, similar to that of FIG. 1, however showing the penis in a flexed condition.
Figure 3:
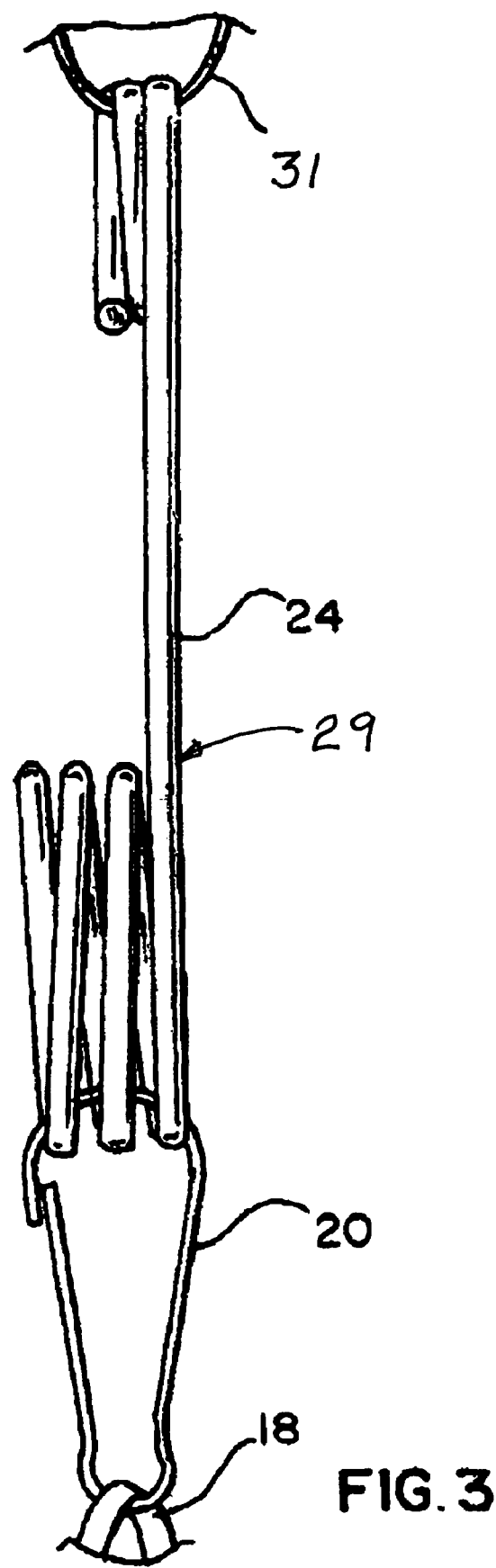
FIG. 3 is a cross-sectional view taken along Line 3-3 of FIG. 1.

Further shown in FIG. 1 is a weight member 16, which in a simple embodiment can comprise a weighted bag, and which through connecting means 18, is connected to a clip 20 which, as is shown in FIG. 3, enables attachment of weight member 16 to a central spring section 29A of spring 29. In accordance with the configuration of the invention 10 shown in FIG. 1, it is seen that the weight member 16 is positioned along a vertical line that substantially bisects the horizontal distance between pads 27 and 28. It is to be noted that a torsion effect of central spring section 29A is such that lever arms 24 and 25 thereof may rotate, or angularly oscillate in accordance with contractions, flexures or other motions of the erect penis in attempting to overcome the weight contained within bag 16. This effect may be more fully appreciated with reference to FIG. 2 in which, responsive to a contraction of the pubococcygeus muscle, penis 14 is elevated thereby causing lever arms 24 and 25 to bend or rotate and to thereby decrease the angle A between the lever arms. Such action will also result in the weight member 16 being moved or repositioned to the approximate center of the horizontal distance between pads 27 and 28.

As may be further appreciated, exercises in the use of the present invention are not limited to the pubococcygeus muscle but, as well, require use of muscles of the lower stomach and other muscles of the pubic area. As such, exercises performed with the inventive device will also result in a tighter and flatter stomach. Further, oscillation of the angle A, also termed the "bounce effect" of the spring 29, confers various biomechanical advantages, a result of which is to strengthen and enlarge the entire penis.

Figure 1B:
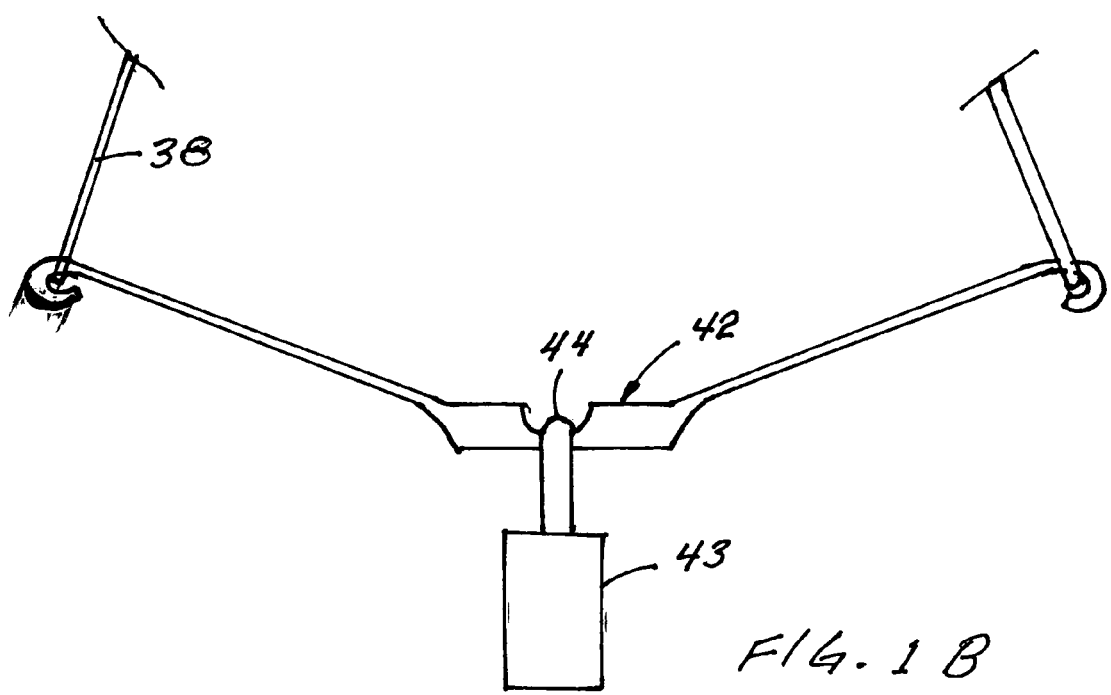
FIG. 1B illustrates an embodiment using a cantilever spring in place of the spring member shown in FIG. 1

It is to be appreciated that central spring 29 and its lever arms 24 and 25 may be formed of various materials including metal wire and plastic. Also, a helical torsion spring, helical extension spring, torsion bar spring, as well as various other types of springs which provide flexural resilience may be suitable to the present application. In this regard, FIG. 1B illustrates one such alternative embodiment of spring 29. In this embodiment, a relatively simple cantilever spring 42 is employed. A detent at the axial center of the spring 42 allows for the hanging of a weight 43 having a hook member 44 integrally or removably attached to the weight 43. Of course, the mass of the weight member 16 or 43 as well as the strength of the spring 29 or 42 are optional and determinable in accordance standard engineering principles.

In the embodiment of FIG. 1, it has been found that the length of lever arms 24 and 25 should preferably be in a range of about 5 to about 8 centimeters, and that the length of said flexible pads 27 and 28 should be in a range of about 8 to about 15 centimeters and have a width in a range of about 2 to about 4 centimeters. The total length of flexible cords 30 and 31 is preferably in a range of about 30 to about 50 centimeters. With respect to weights provided within weighted bag 16, selectable weights, preferably in the form of metal balls, marbles or water weights may be placed therein, the same having an aggregate weight in a range of about 15 to about 500 grams.

It is to be further noted that retaining means 26 and 22 of respective lever arms 24 and 25 need not comprise a loop as is shown in FIGS. 1-3 but, in a given embodiment, may comprise any geometry or mechanical means that can secure the center of respective cords 30 and 31 to respective ends of lever arms 24 and 25.

A program using the above-described device would, typically, comprise the following steps:

1. Begin session with a complete erection.
2. In a standing or sitting position, and with feet 60 to 75 cm apart, tighten abdominal muscles, knees slightly bent, shoulders back, thrusting pelvis and penis area outward/forward.
3. Start-out light with the bag weight being approximately between 70 to 140 gm to warm up, then add more weight as needed during the session.
4. Place straps on penis 14, one strap at base of shaft and the other strap approximately 13 mm behind the glans 15.
5. Continue stimulation to glans 15 for a continued erection during lift/flex reps and hold back your ejaculation throughout the session.
6. Begin to lift/flex penis (penis will lift only about 13 to 19 mm upward with each rep) keeping your penis as rigid as possible during each set of six (6) reps.
7. Finish last rep with a 15-30 second hold (use secondhand timer for each hold); rest, then re-establish your erection and repeat the above at least three (3) sets per session daily and continue until you are unable to keep your erection.
8. For best result, perform one complete session of three (3) sets daily, 3 to 4 times a week, at least 10-15 minutes.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

I claim:

1. A male exercise device adapted to be applied to a penis having a longitudinal axis, comprising
   at least one strap, being flexible, at least in part, in a direction perpendicular to the longitudinal axis of said penis,
   at least two elongated members each being attachable at one end to said at least one strap,
   a spring member having a first and a second end, a second end of each of said at least two elongated members being respectively attachable to said first and second ends of said spring, and
   a weight member attachable to said spring member for providing a resistive weight for the penis to overcome.

2. The apparatus of claim 1 wherein said weight member depends from said spring member.

3. The apparatus of claim 1 wherein said at least two elongated members are flexible and depend from said at least one strap.

4. The apparatus of claim 1 wherein said at least two elongated members are semi-flexible and depend from said at least one strap.

5. The apparatus of claim 1 wherein said at least two elongated members are substantially rigid and depend from said at least one strap.

6. The apparatus of claim 1 wherein said at least one strap is flexible.

7. The apparatus of claim 1 wherein said spring member comprises a first lever arm and a second lever arm with a central section therebetween.

8. The apparatus of claim 7 wherein weight member is attachable to said central section.

9. The apparatus of claim 7 wherein said lever arms are flexible relative to said central section.

10. The apparatus of claim 1 wherein said spring member comprises an elongated cantilever spring having a first lever arm and a second lever arm with a central section therebetween.

11. The apparatus of claim 10 wherein said lever arms are flexible relative to said central section.

12. A male exercise device adapted to be attached to a relatively stiff elongated member that can pivot from a horizontal position to an angled position above the horizontal position, comprising
    at least one strap configured to wrap around said relatively stiff elongated member,
    at least two elongated members each being and being attached at one end to said at least one strap and being spaced along a length of said elongated member,
    a spring member having a first and a second end, a second end of each of said at least two elongated members being respectively attachable to said first and second ends of said spring,
    said spring member comprising a first lever arm and a second lever arm with a central section therebetween, said lever arms being flexible relative to said central section, and
    a weight member attachable to said spring member for providing the male exercise device with a resistive force to be overcome by the erect penis.

13. The apparatus of claim 12 wherein oscillating movement of said relatively stiff member between the horizontal position and the angled position above the horizontal position causes a deflection of said lever arms and a bounce of the weight member.

14. A male exercise device adapted to be attached to a relatively stiff erect penis having muscles, said muscles allowing said penis to pivot from a horizontal position to an angled position above the horizontal position, said muscles capable of being strengthened, comprising
    at least one strap configured to wrap around said relatively stiff elongated member,
    at least two elongated members each being and being attached at one end to said at least one strap and being spaced along a length of said elongated member,
    a spring member having a first and a second end, a second end of each of said at least two elongated members being respectively attachable to said first and second ends of said spring,
    said spring member comprising a first lever arm and a second lever arm with a central section therebetween, said lever arms being flexible relative to said central section, and
    an exercising resisting force weight member attachable to said spring member.

15. The apparatus of claim 14 wherein oscillating movement of said relatively stiff member between the horizontal position and the angled position above the horizontal position causes a deflection of said lever arms and a bounce of the weight member.

* * * * *